United States Patent [19]

Hashimoto et al.

[11] Patent Number: 4,675,161
[45] Date of Patent: Jun. 23, 1987

[54] INDICATOR FOR DETECTION OF THERMAL HISTORY

[75] Inventors: Harumi Hashimoto, Ashiya; Isamu Hirano, Ikeda, both of Japan

[73] Assignee: Sakata Shokai, Ltd., Osaka, Japan

[21] Appl. No.: 566,677

[22] Filed: Dec. 29, 1983

[30] Foreign Application Priority Data

Dec. 29, 1982 [JP] Japan ................. 57-234790

[51] Int. Cl.$^4$ ............ G01K 11/12; G01N 31/22
[52] U.S. Cl. ................... 422/56; 116/207; 116/216; 374/160; 374/162; 422/57; 422/58; 428/321.3; 428/321.5; 428/913; 436/1; 436/2; 436/93; 436/127; 436/147
[58] Field of Search ........... 116/206, 207, 216, 217, 116/219; 374/160, 161, 162; 252/962; 422/55, 56, 58, 34, 236; 436/1, 2, 93, 142, 147; 427/413, 321.5, 321.3

[56] References Cited

U.S. PATENT DOCUMENTS

| | | | |
|---|---|---|---|
| 2,967,785 | 1/1961 | Allen et al. | 428/913 |
| 3,076,721 | 2/1963 | Coles | 428/913 |
| 3,078,182 | 2/1963 | Crone, Jr. et al. | 428/913 |
| 3,239,366 | 3/1966 | Miller et al. | 428/913 |
| 3,317,433 | 5/1967 | Eichel | 428/321.5 |
| 3,615,972 | 10/1971 | Morehouse, Jr. | 428/321.5 |
| 3,695,903 | 10/1972 | Telkes et al. | 428/913 |
| 3,895,523 | 7/1975 | Nollen | 374/162 |
| 4,015,937 | 4/1977 | Miyamoto | 436/93 |
| 4,230,808 | 10/1980 | Pietersen | 428/321.3 |

Primary Examiner—Michael S. Marcus
Attorney, Agent, or Firm—Frishauf, Holtz, Goodman & Woodward

[57] ABSTRACT

An indicator comprising azo dye(s), epoxy compound(s) and a separating membrane can be utilized for detection of the completion of thermal sterilization treatment in the medical field and also for thermal inspection in such various fields as testing, instrumentation and the like. The indicator can be used also for detection of the completion of alkylene oxide gas sterilization treatment by ethylene oxide gas or the like.

22 Claims, No Drawings

INDICATOR FOR DETECTION OF THERMAL HISTORY

FIELD OF THE INVENTION

The present invention relates to an indicator useful for detection of thermal history. More particularly, the present invention relates to an indicator which can be utilized for detection of the completion of thermal sterilization treatment in the medical field and also for thermal inspection in such various fields as testing, instrumentation and the like.

DESCRIPTION OF PRIOR ART

In the medical field, it is important that medical and surgical instruments and materials be sterilized prior to their use. As practical methods for sterilization, there are now used a thermal sterilization method wherein sterilization is made by a wet heat so-called high pressure steam sterilization or steam sterilization or dry heat as well as a gas sterilization method wherein sterilization is made by a gas of an alkylene oxide such as ethylene oxide or the like.

In carrying out these sterilization methods, the instruments and/or materials to be sterilized are placed in a sterilizer and are sterilized in accordance with a predetermined sterilization condition. At this time, it is not sufficient to know the completion of sterilization treatment by the meter(s) of the sterilizer only. As a criterion for knowing the completion, there are generally used various indicators. That is, an indicator is placed in a sterilizer together with the instruments and materials to be sterilized and a change of the indicator is used as a criterion for the completion of the sterilization.

There are two types of indicators, namely, biological indicators and chemical indicators. In the former indicators, it is necessary that, after sterilization treatment, extinction of germ spores or the like be confirmed by the culture of the germ, and hence their use is limited to special applications. In sterilization treatments at hospitals and the like, the latter indicators are widely used for their easier handling.

The present invention relates to an indicator for detection of the completion of thermal sterilization. Chemical indicators for thermal sterilization are disclosed in Japanese Patent Publication Nos. 4650/1970, 2325/1977 and 5996/1978, Japanese Patent Public Disclosure (Laid-open Publication) Nos. 95034/1975 and 106308/1979, etc. However, almost all of the conventional thermal indicators are too sensitive to the temperatures to which these indicators are exposed and, when they reach particular temperatures, they cause complete color changes momentarily. Both those indicators used for detection of the completion of thermal sterilization treatment in the medical field and those used in various testing, instrumentation, and similar applications for detection of thermal history are required to give color changes matching the accumulation of the temperature and the time period in which the indicators have been exposed. Thus, the completion of sterilization and the effect of thermal history can not be confirmed reliably. Almost all of the conventional thermal indicators were not satisfactory in these respects. Further, some of the conventional indicators such as, for example, the indicator disclosed in Japanese Patent Publication No. 4690/1975 had a limitation in terms of the environment of sterilization treatment having the drawback of being usable, for example, only in an alkaline environment. Furthermore, some others gave obscure color changes in sterilization treatment and the completion of sterilization treatment was difficult to judge.

SUMMARY OF THE INVENTION

The primary object of this invention is to provide an indicator which can give a distinct color change and can control the reaction temperature of color change.

Another object of this invention is to provide an indicator which can be utilized for detection of the completion of thermal sterilization treatment in the medical field and also for thermal inspection in such various fields as testing, instrumentation and the like.

Other objects and advantages of this invention will clearly be understood from the following description.

The present invention provides an indicator which is characterized by being structured in such a way that at least one azo dye represented by the general formula

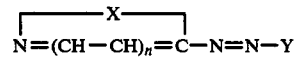

wherein n is 0 or 1, X is a residue of a bivalent group containing a sulfur atom and/or nitrogen atom(s) or a residue of a bivalent group of 5-ring or 6-ring containing nitrogen atom(s), and both of these residues being able to have undissociative groups as substituents, and Y is an aniline derivative residue whose para position can be coupled or an enamine residue, both of these residues also being able to have undissociative groups as substituents, and at least one epoxy compound which is fluid or solid at the room temperature are adjacent through a separating membrane having a melting or softening point of 50° to 300° C., composed of a heatmelting or heat-softening material which does not react with said epoxy compound, and having a thickness of 0.5 to 200μ.

DESCRIPTION OF THE PREFERRED EMBODIMENT

Azo dyes used in the indicator of the present invention are those represented by the above general formula and are produced by the ordinary synthesis between a diazo component and a coupling component. Structural formulas of representative azo dyes are as follows.

As the structural formulas of azo dyes wherein X has been given specifically, the following are illustrated:

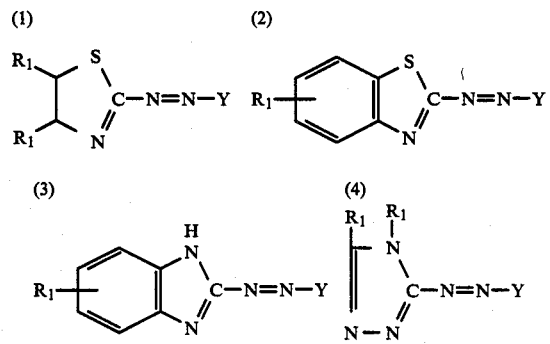

(5) 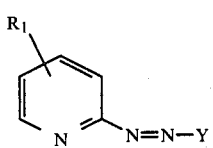

(6) 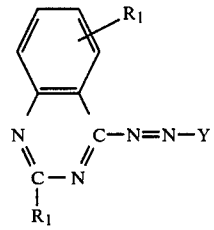

(7) 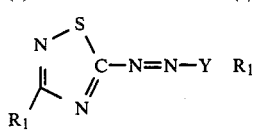

(8) 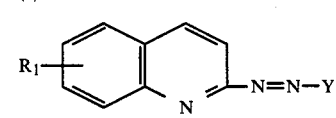

(9) 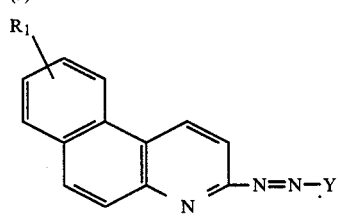

In the above structural formulas (1) to (9), $R_1$ is a hydrogen or halogen atom or an undissociative substituent. The undissociative substituent includes lower alkyl groups such as methyl group, ethyl group, propyl group, butyl group and the like; lower alkoxy groups such as methoxy group, ethoxy group, propoxy group, butoxy group and the like; lower hydroxyalkyl groups such as ethylol group, methylol group and the like; alkoxyalkyl groups such as methoxymethyl group and the like; aromatic groups such as phenyl group, phenoxy group, benzyl group and the like; nitro group, acylamino group; and so forth. A plurality of hydrogen atoms present in one molecule may be substituted by substituents which are the same or different.

As the structural formula of azo dyes wherein Y is an aniline derivative residue whose para position can be coupled, the following is illustrated:

(10) 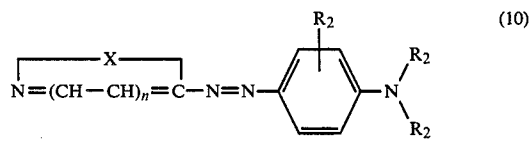

As the structural formulas of azo dyes wherein Y is an enamine residue (enamine refers to compounds each having within their molecules a group represented by $>C=C-N<$), the following are illustrated:

(11) 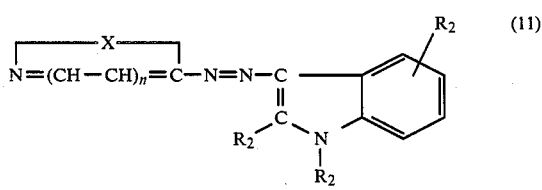

(12) 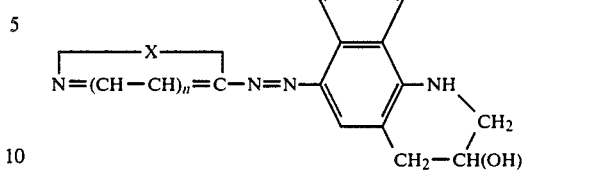

(13) 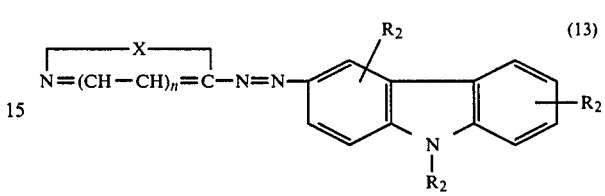

In the structural formulas (10) to (13), $R_2$ is the same atom or substituent as those of $R_1$. In the formula (10), two $R_2$s connecting with the same nitrogen may be the same or different atoms or substituents. As $R_2$ in each of the formulas (10) to (13), a plurality of hydrogen atoms present in one molecule may be substituted by substituents which are the same or different, as in the case of $R_1$.

As the epoxy compound which is fluid or solid at the normal temperature, there are mentioned polyethylene oxides; polypropylene oxides; polybutylene oxides; polyepichlorohydrins; styrene oxide; glycidyl phenyl ether; diepoxy or triepoxy compounds obtained by the reaction between a polyhydric alcohol such as, for example, glycol, glycerine, bisphenol A or the like and epichlorohydrin; epoxy compounds of a type of a glycidyl ester of an acid such as acrylic acid, methacrylic acid, acetic acid, lauric acid, myristic acid, palmitic acid, stearic acid, oleic acid, adipic acid, maleic acid or the like; epoxy resins of glycidyl ester type, bisphenol A type, bisphenol F type, phenolic novolak type and polyalcohol ether type; etc.

As specific examples of the heat-melting or heat-softening material constituting the separating membrane, there are illustrated resins soluble in organic solvents such as vinyl acetate resins, vinyl chloride resins, ethylene-vinyl acetate copolymer resins, vinyl chloridevinyl acetate copolymer resins, styrene resins, acrylic resins, polyamide resins, alkyd resins, petroleum resins, coumarone-indene resins, cyclized rubbers, urethane resins and the like; as well as resins soluble or dispersible in water such as acrylic resins, styrene-acryl copolymer resins, styrene-maleic acid copolymer resins, maleic acid resins, rosin modified maleic acid resins, polyvinyl alcohols, polyvinyl acetals, zein, casein, CMC, shellac, acrylic emulsions, styrene-acryl emulsions, styrene-shellac emulsions, vinyl acetate emulsions and the like.

These resins are selected individually or as a mixture of two or more with attention being paid to their melting or softening points.

When the above mentioned resins have a melting point lower than 50° C, their function as a separating membrane between an azo dye and an epoxy compound becomes insufficient and indicators using such resins have no reliability because they may possibly cause reaction and color change during storage. It is desirable from the standpoint of heat resistance of azo dyes that the above resins have a melting point of 300° C. or lower.

The separating membrane material is required to have another essential property of being able to form a continuous film in the form of a thin layer. In the thermal indicator of the present invention, it is necessary that the separating membrane has a film thickness of 0.5 to 200μ in its dry state and yet is able to exhibit its required function. When the separating membrane has a dry film thickness of less than 0.5μ, it is difficult to keep the film continuity and the separating membrane has insufficient strength. When the separating membrane has a dry film thickness of more than 200μ, it is difficult to form the separating membrane and, even if formed, the membrane is liable to become cracked, etc. Further, when the separating membrane has too great a film thickness, reaction between an azo dye and an epoxy compound becomes difficult and it becomes impossible to obtain an intended color change under a predetermined condition.

In place of the above mentioned resins or in combination with them, waxes can be used.

As these waxes, there are mentioned animal waxes which are separated from animal oils, such as bees wax, shellac wax and the like; vegetable waxes which are separated from vegetable oils, such as carnauba wax and the like; mineral waxes which are separated from mineral oils, such as montan wax and the like; petroleum waxes such as paraffin wax, microcrystalline wax and the like; and synthetic waxes such as polyalcohol esters of higher fatty acids, higher amines, higher amides, condensation products between a fatty acid and an amine, condensation products between an aromatic and an amine, synthetic paraffins, chlorinated paraffins, metal salts of higher fatty acids, and the like.

Besides, PVA, casein, gelatine, starch, methyl cellulose, ethyl cellulose, carboxymethyl cellulose and nitrocellulose can also be used in combination with the above mentioned resins.

In production of the thermal indicator of the present invention, selection of the melting or softening point of a resin or resin mixture as a separating membrane becomes important. In order to obtain a complete color change matching a given condition of thermal treatment, it is necessary to select a resin or the like having a melting or softening point in the range between a temperature 10° C. lower than an intended thermal treatment temperature and a temperature 10° C. higher than the treatment temperature. However, there are cases in which melting or softening points of resins or the like change depending upon the film thickness, hardness and the properties of the separating membrane and, therefore, it is necessary to select a resin or the like after conducting an actual thermal treatment and confirming reaction rate and color changing property.

When the indicator of the present invention is used as an indicator for dry heat sterilization treatment, because the ordinary temperature of dry heat sterilization treatment is 140° to 250° C., it is necessary to select, as a separating membrane material, a resin or the like having a melting or softening point in the temperature range of about 130° to 260° C.

In the case of wet heat sterilization treatment, because the ordinary treatment temperature is 115° to 135° C., it is necessary to select, as a separating membrane material, a resin having a melting or softening point in the temperature range of about 105° to 145° C.

In the thermal indicator of the present invention, the color change is generally allowed to occur according to the melting or softening point of the separating membrane resin. However, when a thermal indicator using an aqueous resin as a separating membrane material is applied for wet heat sterilization, the color change shows very unique behavior. That is, under wet heat sterilization conditions, color change occurs at a temperature much lower than the above melting or softening point. The reason for this is presumed to be that, when an aqueous resin used as a separating membrane is heated to a certain temperature level, steam used for wet heat sterilization acts so as to allow an azo dye and an epoxy compound to react with each other. Consequently, by using, for the separating membrane, an aqueous resin having a melting or softening point higher than the ordinary wet heat sterilization temperature of 115° to 135° C., for example, a melting or softening point of about 125° to 170° C., color change at 115° to 135° C. occurs when steam is present and a wet heat sterilization can be reliably confirmed.

When the indicator of the present invention is used as a testing paper for thermal history, it is necessary to select the melting or softening point of the separating membrane resin after thorough consideration of the temperature condition to be measured.

Hereinunder, the process for producing the thermal indicator of the present invention will be explained.

As aforementioned, the indicator according to the present invention comprises, as essential components, at least one azo dye, at least one epoxy compound and a separating membrane material. Using these components, an indicator can be produced in accordance with the following processes.

Firstly, there is produced an ink containing an azo dye as one component of coloring agents. This ink can be easily prepared by those skilled in ink or coating production. One example of this production is as follows.

Azo dyes specified in the present invention are soluble in alcohol type solvents. Therefore, as a binder, there are used resins which are soluble in the above solvents used as a main solvent or co-solvent, such as, for example, nitrocellulose, butyral resins, polyamide resins, rosin modified maleic acid resins, acrylic resins, styrene resins, styrene-maleic acid resins, shellac and the like. As necessary, other dyes or pigments than azo dyes are also used. An azo dye and said other components are conventionally mixed and thereby forming a solution, namely, an ink is obtained.

Microcapsules containing an epoxy compound specified by the present invention can be produced by a conventional known method. They can be produced, for example, by the coacervation method described in U.S. Pat. No. 2,800,457, U.S. Pat. No. 2,800,458, etc., the interfacial polymerization method described in BP No. 990443, U.S. Pat. No. 3,287,154, etc., the method desceibed in U.S. Pat. No. 3,418,250, U.S. Pat. No. 3,660,304, Japanese Patent Publication No. 23165/1972, U.S. Pat. No. 3,726,804, etc., or the method wherein an epoxy resin powder is dispersed in a solution of a separating membrane resin and the dispersion is spray-dried.

The microcapsules produced by the above method are dispersed in the aforementioned ink whereby a thermal indicator in the form of liquid dispersion is obtained. A thermal indicator coated on a substrate in a thin layer can be obtained by coating the above liquid dispersion on a substrate such as a paper film or the like. Further, a thermal indicator coated on a substrate in two or three layers can also be produced. In this case, a coating agent containing an epoxy compound and a coating agent containing a separating membrane material are produced first, respectively. If necessary, these coating agents may contain a solvent, other film-forming material and a plasticizer. Then, in the case of coating in two layers, the aforementioned microcapsules are dispersed in the coating agent containing a separating membrane material to obtain a dispersion and thereafter there are coated, on a substrate such as a paper, film or the like, an ink and the dispersion in this order. In the case of coating in three layers, there are coated, on a substrate such as a paper, film or the like, an ink, the coating agent containing a separating membrane material and the coating agent containing an epoxy compound, in this order.

As the catalyst for controlling the reaction between an azo dye and an epoxy compound, an acid catalyst such as phosphoric acid, p-toluenesulfonic acid, citric acid, maleic acid, malonic acid or the like is desirable. Further, addition of a filler such as, for example, silica, barium sulfate, clay, magnesium carbonate, calcium carbonate or the like is desirable.

The above additives can be added to a system containing an azo dye and/or a system containing an epoxy compound.

The above three processes for producing the indicator of the present invention show some embodiments of the present invention. Of course, other indicators such as using microcapsules containing an azo dye specified by the present invention can also be utilized.

The indicator of the present invention must have a constitution in which a system containing an azo dye and a system containing an epoxy compound are present in a noncontact state through a separating membrane. However, various constitutions can be used depending upon the application purpose of the indicator. Further, the indicator of the present invention can give a color change matching an intended temperature condition and treatment time of sterilization by appropriately selecting the melting or softening point of a separating membrane resin or the like as well as the thickness of the membrane.

The indicator of the present invention can be used also for detection of the completion of alkylene oxide gas sterilization treatment by alkylene oxide gas such as ethylene oxide gas or the like. Accordingly, the indicator of the present invention can detect the completion of thermal sterilization as well as the completion of gas sterilization.

The indicator of the present invention can be used in various forms such as a thermal indicator label or tape, a thermal indicator test piece and a bag with thermal indicator.

Hereinunder, the present invention will be explained in more detail by way of Examples. However, these Examples are only limited embodiments of the present invention and in no way restrict the present invention. In the Examples, "part" and "percent" represent "by weight".

Ink (1) Production

20 Parts of a butyral resin [Denka-butyral (Trademark) N-2000 L manufactured by Denki Kagaku Kogyo Kabushiki Kaisha] was dissolved in a mixture of 20 parts of toluene, 48 parts of methanol and 10 part of Methyl Cellosolve (Trademark) to produce an ink vehicle. To this vehicle was added 1 part of the following azo dye No. 1 and 1 part of malonic acid as a catalyst to obtain an ink (1) of yellow color.

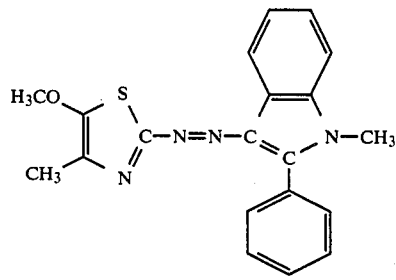

No. 1

Ink (2) Production

Using 30 parts of methanol, 20 parts of isopropanol, 10 parts of Methyl Cellosolve (Trademark), 38 parts of a rosin modified maleic acid resin [Teskid (Trademark) MRM-62 manufactured by Tokushima Seiyu Co., Ltd.], 1 part of the following azo dye No. 2 and 1 part of maleic acid as a catalyst, an ink (2) of red color was produced in the same manner as in Example 1 for ink production.

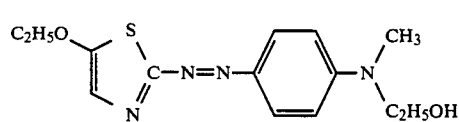

No. 2

Inks (3) to (13) Production

Using 40 parts of toluene, 15 parts of methanol, 10 parts of Methyl Cellosolve (Trademark), 30 parts of a polyamide resin [Polyamide (Trademark) S-40E manufactured by Sanyo Chemical Industries, Ltd.], 1 part of either of the following azo dyes Nos. 3 to 13, 1 part of p-toluenesulfonic acid as a catalyst and 3 parts of colloidal silica as a filler, [Aerosil (Trademark) R-972 manufactured by Nippon Aerosil Co., Ltd.], inks (3) to (13) were produced in the same manner as in Example 1 for ink production.

| Ink production | Dyes | | Color |
|---|---|---|---|
| ink 3 | No. 3 | 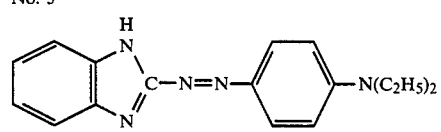 | red |
| ink 4 | No. 4 | | yellow |

| Ink production | Dyes | | Color |
|---|---|---|---|
| | -continued | | |
| | 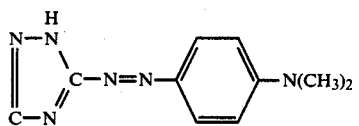 | | |
| ink 5 | No. 5 | | yellow |
| | 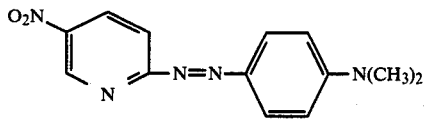 | | |
| ink 6 | No. 6 | | yellow |
| | 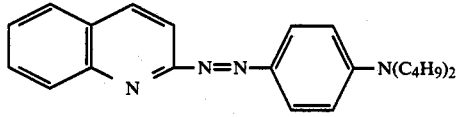 | | |
| ink 7 | No. 7 | | red |
| | 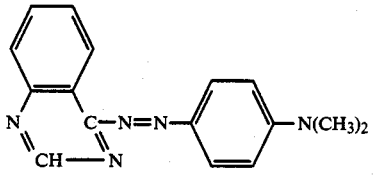 | | |
| ink 8 | No. 8 | | red |
| | 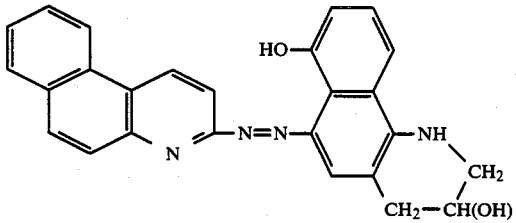 | | |
| ink 9 | No. 9 | | yellow |
| | 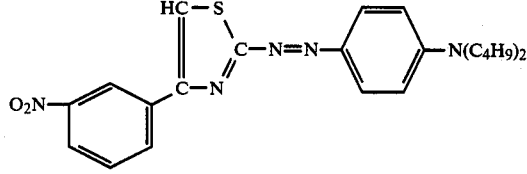 | | |
| ink 10 | No. 10 | | red |
| |  | | |
| ink 11 | No. 11 | | yellow |

| Ink production | Dyes | Color |
|---|---|---|
| ink 12 | No. 12 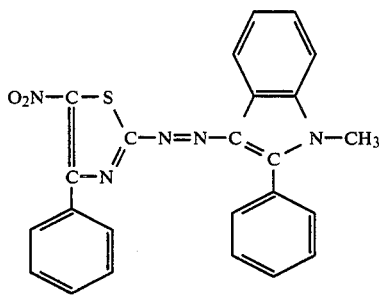 | yellow |
| ink 13 | No. 13 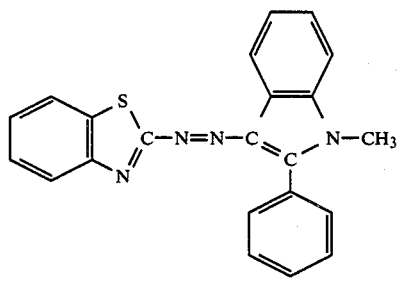 | red |
| | 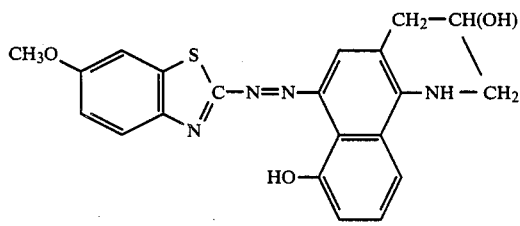 | |

Ink (14) Production

To an ink vehicle consisting of 30 parts of methanol, 20 parts of isopropyl alcohol, 10 parts of Methyl Cellosove (Trademark) and 30 parts of a rosin modified maleic acid resin (MRM-62) was added 10 parts of a yellow pigment of diazo yellow type, and they were kneaded and dispersed to produce a pigment ink. 10 Parts of this pigment ink was mixed with 90 parts of the aforementioned ink (2) to obtain an ink (14) of red color.

Production of a Coating Agent (1-1) as Separating Membrane

In 80 parts of a mixed solvent consisting of 45 parts of toluene, 25 parts of methanol and 10 parts of ethyl acetate was dissolved 20 parts of a polyamide resin [S-40E manufactured by Sanyo Chemical Industries, Ltd., m.p. 110° C.] to produce a coating agent (1-1).

Production of a Coating Agent (1-2) as Separating Membrane

In 80 parts of a mixed solvent consisting of 30 parts of isopropyl alcohol, 20 parts of ethyl acetate and 30 parts of ethanol was dissolved 20 parts of a maleic acid resin [Markid (Trademark) 3002 manufactured by Arakawa Chemical Industries, Ltd., m.p. 165° to 185° C.] to produce a coating agent (1-2).

Production of a Coating Agent (1-3) as Separating Membrane

20 Parts of a petroleum resin [Hi-Resin (Trademark) QP manufactured by Toho Petroleum Resin Co., Ltd., m.p. 130° C.] was dissolved in 80 parts of a mixed solvent consisting of 30 parts of toluene, 20 parts of ethyl acetate and 30 parts of isopropyl alcohol to produce a coating agent (1-3)

Production of a Coating Agent (1-4) as Separating Membrane

20 Parts of an acrylic resin [Joncryl (Trademark) 67 manufactured by S. C. Johnson & Son Inc., m.p. 143° C.] was dissolved in 80 parts of a mixed solvent consisting of 60 parts of isopropyl alcohol and 20 parts of ethyl acetate to produce a coating agent (1-4).

Production of a Coating Agent (1-5) as Separating Membrane

20 Parts of a maleic acid resin [Beckacite (Trademark) 1120 manufactured by Japan Reichhold Chemical Inc., m.p. 120° C.] was dissolved in 80 parts of a mixed solvent consisting of 30 parts of toluene, 20 parts of ethyl acetate and 30 parts of isopropyl alcohol to produce a coating agent (1-5).

Production of a Coating Agent (1-6) as Separating Membrane

30 Parts of an acrylic resin Joncryl (Trademark) 67 manufactured by S.C. Johnson & Son Inc., m.p. 143° C.], 6 parts of 28% aqueous ammonia solution, 10 parts of isopropyl alcohol and 54 parts of water were mixed. They were heated to about 70° C., whereby a coating agent (1-6) was produced.

Production of a Coating Agent (1-7) as Separating Membrane

30 Parts of a maleic acid resin [Markid (Trademark) No. 32 manufactured by Arakawa Chemical Industries, Ltd., m.p. 130° C.], 6 parts of 28% aqueous ammonia solution, 10 parts of isopropyl alcohol and 54 parts of water were mixed and heated to about 70° C., whereby a coating agent (1-7) was produced.

Production of a Coating Agent (1-8) as Separating Membrane

30 Parts of a styrene/maleic acid resin [SMA 2000 manufactured by Alco Chemical Co., m.p. 150° C.], 9 parts of 28% aqueous ammonia solution, 10 parts of isopropyl alcohol and 51 parts of water were mixed and heated to about 70° C., whereby a coating agent (1-8) was produced.

Production of a Coating Agent (1-9) as Separating Membrane

20 Parts of an acrylic resin [Paraloid (Trademark) A-11 manufactured by Rohm and Haas Co., m.p. 140° C.] was dissolved in a mixed solvent consisting of 20 parts of ethanol, 30 parts of isopropyl alcohol and 30 parts of ethyl acetate to produce a coating agent (1-9).

Production of a Coating Agent (1-10) as Separating Membrane

In a reactor equipped with a thermometer, a stirrer, a tube for nitrogen gas introduction and a reflux condenser were placed 450 parts of a deionized water and 10 parts of a surfactant as emulsifier [Aerosol (Trademark) A-102 manufactured by American Cyanamid Co.]. Thereto was added a solution consisting of 1.25 parts of potassium persulfate and 30 parts of a deionized water. The resulting mixture was heated to 60° C. with introducing nitrogen gas thereto. Using a polymerizable vinyl monomer mixture consisting of 275 parts of methyl methacrylate, 25 parts of methacrylic acid, 200 parts of butyl acrylate and 5 parts of N-dodecylmercaptan, emulsion polymerization was conducted in the above reactor in accordance with the ordinary method. Then, the content in the reactor was neutralized with triethanolamine to obtain an acrylic emulsion having a softening point of about 150° C. This emulsion was used as a coating agent (1-10).

Production of a Coating Agent (2-1) Containing an Epoxy Compound

20 Parts of an epoxy resin as epoxy compound [Epiclon (Trademark) 2050 manufacutured by Dainippon Ink & Chemicals, Inc., m.p. 84° C.] was dissolved in 80 parts of a mixed solvent consisting of 40 parts of methyl ethyl ketone (MEK) and 40 parts of ethyl acetate to produce a coating agent (2-1).

Production of a Coating Agent (2-2) Containing an Epoxy Compound

20 Parts of an epoxy resin as epoxy compound [Epiclon (Trademark) 7050 manufactured by Dainippon Ink & Chemicals, Inc., m.p. 130° C.] was dissolved in 80 parts of the same mixed solvent as used in production of the coating agent (2-1), whereby a coating agent (2-2) was produced.

Production of a Coating Agent (2-3) Containing an Epoxy Compound

20 Parts of an epoxy resin as epoxy compound [Epiclon (Trademark) N-695 manufactured by Dainippon Ink & Chemicals, Inc., m.p. 95° C.] was dissolved in 80 parts of the same mixed solvent as used in production of the coating agent (2-1), whereby a coating agent (2-3) was produced.

Production of a Coating Agent (2-4) Containing an Epoxy Compound

20 Parts of an epoxy resin as epoxy compound [Epiclon (Trademark) N-755 manufactured by Dainippon Ink & Chemicals, Inc., m.p. 70° C.] was dissolved in 80 parts of the same mixed solvent as used in production of the coating agent (2-1), whereby a coating agent (2-4) was produced.

Microcapsule (1) Production

10 Parts of an acrylic resin [Paraloid (Trademark) A-11 manufactured by Rohm & Haas Co.] was dissolved in 90 parts of a mixed solvent consisting of 20% of ethanol, 40% of isopropyl alcohol and 30% of ethyl acetate. Into the resulting solution was mixed and dispersed 50 parts of a powder of an epoxy resin [Epiclon (Trademark) 7050 of about 400 mesh. This dispersion was made into fine particles by spraying and drying by the use of a spray drier, whereby microcapsules (1) were obtained.

Microcapsule (2) Production

100 Parts of an epoxy resin [Epiclon (Trademark) 1050 manufactured by Dainippon Ink & Chemicals, Inc.] was dissolved in 100 parts of a mixed solvent consisting of 50% of toluene and 50% of MEK to prepare an epoxy resin solution. Separately, 2 parts of a curing agent [Epicure (Trademark) T manufactured by Yuka Shell Epoxy K.K.] was dissolved in 2000 parts of 2% aqueous polyvinyl alcohol (PVA) solution.

Into this aqueous solution was dropped the above epoxy resin solution, and they were stirred at the normal temperature to form fine droplets. Then, with keeping the liquid temperature at 80° C., stirring was continued for about 4 hr, whereby microcapsules (2) whose outer shell was in interfacial polymerization product between part of the epoxy resin and the curing agent and which contained the epoxy resin solution was produced.

Microcapsule (3) Production

100 Parts of a liquid epoxy resin [Epiclon (Trademark) 705 manufactured by Dainippon Ink & Chemicals, Inc.] was dropped into 1000 parts of 2% aqueous gum arabix solution containing 5 parts of a curing agent [Epocure (Trademark) T]. They were stirred at the normal temperature to form fine droplets. Then, with keeping the liquid temperature at 80° C., stirring was continued for about 3 hr, whereby microcapsules (3)

containing the liquid epoxy resin was produced in accordance with the interfacial polymerization method.

sterilization to examine the color change of each indicator. All indicators changed from red to blue.

TABLE 2

| Example | Name of coating agent as separating membrane | Name of coating agent containing an epoxy compound | Name of indicator | Condition for wet heat sterilization | | Condition for dry heat sterilization | |
|---|---|---|---|---|---|---|---|
| | | | | Temperature | Time | Temperature | Time |
| 15 | coating agent (1-5) | coating agent (2-4) | indicator (15) | 121° C. | 20 min | — | — |
| 16 | coating agent (1-2) | coating agent (2-2) | indicator (16) | — | — | 165° C. | 2 hr |
| 17 | coating agent (1-3) | coating agent (2-3) | indicator (17) | 132° C. | 10 min | — | — |
| 18 | coating agent (1-4) | coating agent (2-2) | indicator (18) | — | — | 145° C. | 3 hr |

EXAMPLES 1 to 14

Each of the aforementioned inks (1) to (14) was printed on a paper for sterile bag. Then thereon were coated the coating agent (1-1) as separating membrane and the coating agent (2-1) containing an epoxy compound in that order by the use of a gravure coater having 30μ shell depth, whereby indicators (1) to (14) for detecting the completion of thermal sterilization treatment were produced.

Using each indicator, thermal sterilization was conducted under the following conditions and the color change of each indicator are given in the following Table 1.

Conditions of Wet Heat Sterilization Treatment

Steam temperature: 115° C.
Treating time: 30 min.

The following results were obtained.

TABLE 1

| | | | Color change by thermal sterilization treatment | |
|---|---|---|---|---|
| Example | Name of ink | Name of indicator | Before treatment | After treatment |
| 1 | ink (1) | indicator (1) | yellow | red |
| 2 | ink (2) | indicator (2) | red | blue |
| 3 | ink (3) | indicator (3) | red | purple |
| 4 | ink (4) | indicator (4) | yellow | red |
| 5 | ink (5) | indicator (5) | yellow | purple |
| 6 | ink (6) | indicator (6) | yellow | blue |
| 7 | ink (7) | indicator (7) | red | purple |
| 8 | ink (8) | indicator (8) | red | blue |
| 9 | ink (9) | indicator (9) | yellow | green |
| 10 | ink (10) | indicator (10) | red | blue |
| 11 | ink (11) | indicator (11) | yellow | red |
| 12 | ink (12) | indicator (12) | yellow | red |
| 13 | ink (13) | indicator (13) | red | blue |
| 14 | ink (14) | indicator (14) | red | green |

As is obvious from the above results, the indicators according to the present invention gave a distinct color change in the above thermal sterilization treatment.

EXAMPLES 15 to 18

The ink aforementioned (2) was printed on a paper for sterile bag. Then thereon were coated a coating agent as separating membrane and a coating agent containing an epoxy compound (details of both agents are shown in the following Table 2) in that order, whereby indicators (15) to (18) were produced. These indicators were subjected to wet heat sterilization and dry heat sterilization to examine the color change of each indicator. All indicators changed from red to blue.

As is obvious from the above results, indicators matching different thermal sterilization temperatures can be produced by appropriately selecting the softening point or melting point of the resin to be used in a coating agent as separating membrane.

EXAMPLES 19 to 21

20 Parts each of the aforementioned microcapsules (1) to (3) were mixed with 100 parts of the aforementioned ink (2), and they were dispersed to obtain three kinds of microcapsule-containing inks. Each ink was printed on a paper for sterile bag to obtain indicators (19) to (21).

These indicators were subjected to wet heat sterilization treatment (132° C, 10 min), whereby the indicators changed from red to blue.

EXAMPLES 22 to 26

Each of the aforementioned inks (1) to (5) was printed on a paper for sterile bag Then thereon were coated the coating agent (1-6) as separating membrane and the coating agent (2-1) containing an epoxy compound in that order, whereby indicators (22) to (26) for detection of the completion of thermal sterilization were produced.

Each indicator was subjected to thermal sterilization under the following conditions to examine its color change. The results are given in the following Table 3.

Conditions of Wet Heat Sterilization Treatment

Steam temperature: 126° C.
Treating time: 20 min.

TABLE 3

| | | | Color change by thermal sterilization treatment | |
|---|---|---|---|---|
| Example | Name of ink | Name of indicator | Before treatment | After treatment |
| 22 | ink (1) | indicator (22) | yellow | red |
| 23 | ink (2) | indicator (23) | red | blue |
| 24 | ink (3) | indicator (24) | red | purple |
| 25 | ink (4) | indicator (25) | yellow | red |
| 26 | ink (5) | indicator (26) | yellow | purple |

As is obvious from the above results, the indicators according to the present invention gave a distinct color change in the above thermal sterilization treatment. Despite the fact that, in these indicators, the coating agent (1-6) containing an aqueous resin having a melting point of 143° C. was used, the indicators caused a color change in the wet heat sterilization of 126° C. which was considerably lower than 143° C. Thus, these indicators are useful as indicators for wet heat sterilization.

EXAMPLES 27 to 31

The ink (2) was printed on a paper for sterile bag. Then, thereon were coated a coating agent as separating membrane and a coating agent containing an epoxy compound (details of these agents are shown in the following Table 4) in that order, whereby thermal indicators (27) to (31) were produced. These indicators were subjected to wet heat sterilization and dry heat sterilization to examine respective color changes. The results are given in the following Table 4.

TABLE 4

| Example | Name of coating agent as separating membrane | Name of coating agent containing an epoxy compound | Name of indicator | Wet heat sterilization Temperature condition | Wet heat sterilization Color change | Dry heat sterilization Temperature condition | Dry heat sterilization Color change |
|---|---|---|---|---|---|---|---|
| 27 | coating agent (1-6) | coating agent (2-2) | indicator (27) | 126° C. (20 min.) | red to blue | 145° C. (3 hr.) | red to blue |
| 28 | coating agent (1-9) | coating agent (2-2) | indicator (28) | 126° C. (20 min.) | no change | 145° C. (3 hr.) | red to blue |
| 29 | coating agent (1-7) | coating agent (2-3) | indicator (29) | 115° C. (30 min.) | red to blue | 135° C. (3 hr.) | red to blue |
| 30 | coating agent (1-3) | coating agent (2-3) | indicator (30) | 115° C. (30 min.) | no change | 135° C. (3 hr.) | red to blue |
| 31 | coating agent (1-10) | coating agent (2-3) | indicator (31) | 132° C. (10 min.) | red to blue | 135° C. (3 hr.) | no change |

As is obvious from the above results, when indicators (27), (29) and (31) each using an aqeuous resin as a separating membrane resin were subjected to wet heat sterilization treatment, their color change was unique. That is, it occured distinctly even at a temperature much lower than the melting point of the aqueous resin used.

When these indicators (27), (29) and (31) were subjected to dry heat sterilization treatment, their color change occured dependently upon the melting point of the aqueous resin used as a separating membrane resin, like the indicators (28) and (30) in which the aqueous resin was not used. Accordingly, by using an aqueous resin as a separating membrane resin, an indicator can be produced which gives different color change temperatures in dry heat sterilization treatment and wet heat sterilization treatment.

In sterilization, it is desirable to use an aqueous resin as a separating membrane resin.

EXAMPLE 32

Indicators (15), (17) and (20) were subjected to wet heat sterilization, whereby the relation between the color change of each indicator and the time passing before extinction of a reference germ was examined.

The indicator (15) of red color turned bright blue in the wet heat sterilization condition of 121° C. and about 20 min. The indicators (17) and (20) both of red color also turned bright blue in the wet heat sterilization condition of 132° C. and about 10 min.

On the other hand, it is said that the time to extinction of 10,000 to 100,000 spores of a thermostable germ as a reference germ is, in general, about 10 min. at 121° C. and 1 to 2 min. at 132° C. Accordingly, it can be concluded that, when the above indicators according to the present invention turn bright blue, the probability of survival of the above germ is almost zero.

When the above indicators of the present invention show a purple color, their color change is insufficient and accordingly sterilization is also insufficient. It is important that the completion of sterilization be confirmed by a distinct blue color of the above indicators. A blue color of the indicators shows the extinction of a germ. Thus, the above indicators provide a high reliability for confirmation of the extinction of a germ.

The above indicators were also subjected to ethylene oxide sterilization. The results similar to those of the above wet heat sterilization were obtained.

EXAMPLE 33

Indicators (15) to (18) were subjected to color change test by a heat sealing tester to evaluate their performances as a testing paper for thermal history.

Each of the above indicators was subjected to heat sealing for 30 sec. at an applied pressure of 1 kg/cm$^2$, at five temperature points at 5° C. intervals (the center point was set to be the same as the melting or softening point of the resin of the coating agent used as a separating membrane which is the middle layer of the indicator). The extent of the color change of each indicator was different depending upon the temperature point of heat sealing. Presumably, the reaction was accelerated by the applied pressure. However, complete color change was observed at or above the melting or softening point of the resin of the separating membrane and, at lower temperatures, the extent of color change was weaker. This test shows that the indicator of the present invention also possesses a function as a testing paper for thermal history.

What is claimed is:

1. An indicator for detection of thermal history which comprises:
   (a) at least one azo dye selected from the group consisting of

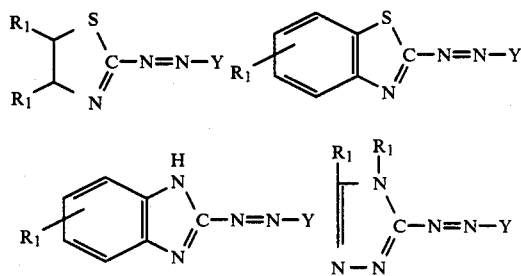

-continued

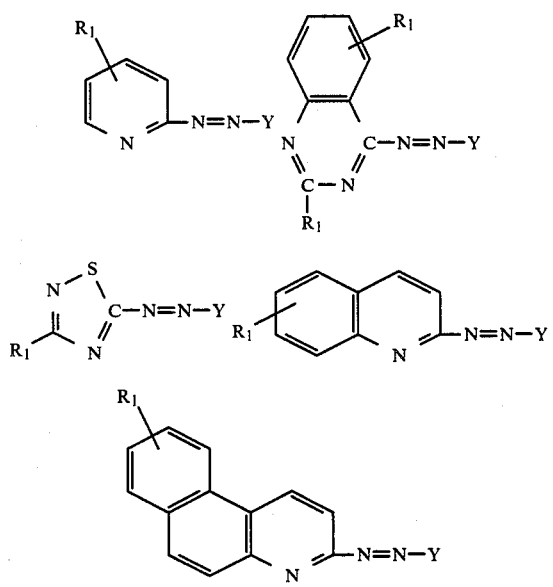

wherein each $R_1$ is a hydrogen or an undissociative substituent selected from the group consisting of halogen atoms, lower alkyl groups, lower alkoxy groups, alkoxy alkyl groups, aromatic groups, nitro group and acylamino group, and Y is a group of the formula

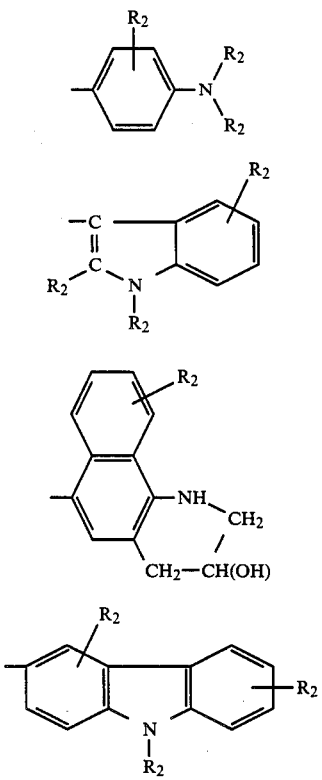

wherein $R_2$ has the same definition as $R_1$;
(b) at least one epoxy compound selected from the group consisting of polyethylene oxides; polypropylene oxides; polybutylene oxides; polyepichlorohydrins; styrene oxide; glycidyl phenyl ether; diepoxy or triepoxy compounds obtained by the reaction between a polyhydric alcohol and epichlorohydrin; epoxy compounds of the type of a glycidyl ester of an acid; and epoxy resins of the glycidyl ester type, bisphenol A type, bisphenol F type, phenolic novolak type and polyalcohol ether type; and (c) a separating membrane having a melting or softening point of 50° to 300° C., composed of a heat-melting or heat-softening material which does not react with said epoxy compound (b), and having a thickness of 0.5 to 200µ;

said element (a) and said element (b) are adjacent through said separating member (c) thereby providing an indicator for detection of thermal history.

2. The indicator according to claim 1, wherein there are coated, on a substrate, the element (a) of at least one azo dye, the element (c) of a separating membrane and the element (b) of at least one epoxy compound in that order and in three layers.

3. The indicator according to claim 1, wherein the azo dye is a member selected from the group consisting of

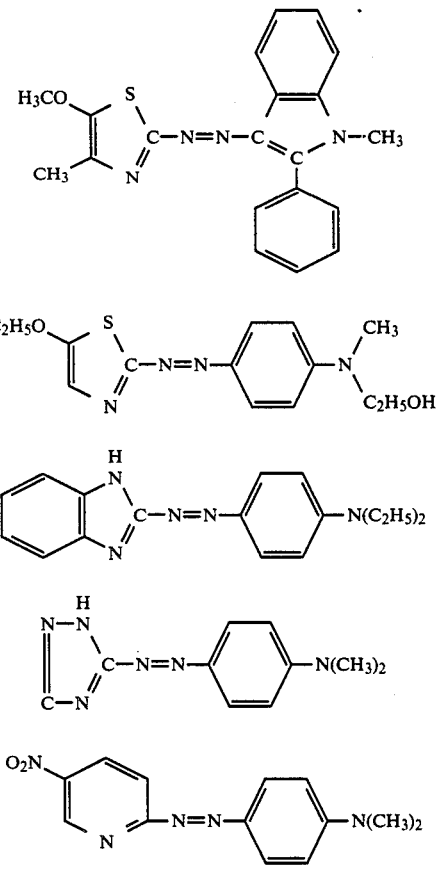

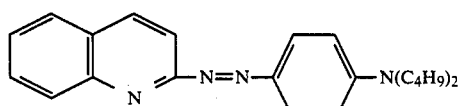

-continued

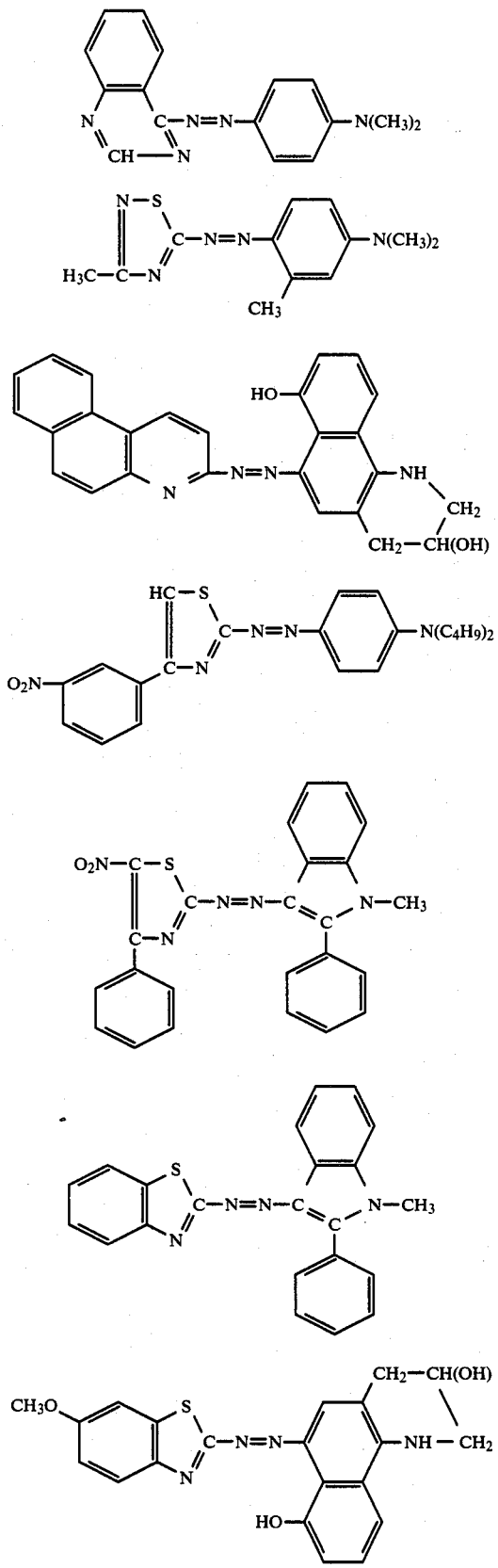

4. The indicator according to claim 1, wherein the epoxy compound is a member selected from the group consisting of; diepoxy or triepoxy compounds obtained by the reaction between a polyhydric alcohol selected from the group consisting of glycol, glycerine and bis-phenol A and epichlorohydrin; epoxy compounds of the type of a glycidyl ester of an acid selected from the group consisting of acrylic acid, methacrylic acid, acetic acid, lauric acid, myristic acid, palmitic acid, stearic acid, oleic acid, adipic acid and maleic acid.

5. The indicator according to claim 1, wherein the element of the separating membrane is a member selected from the group consisting of vinyl acetate resins, vinyl chloride resins, ethylene-vinyl acetate copolymer resins, vinyl chloride-vinyl acetate copolymer resins, styrene resins, acrylic resins, polyamide resins, alkyd resins, petroleum resins, coumarone-indene resins, cyclized rubbers, urethane resins, styrene-acryl copolymer resins, styrene-maleic acid copolymer resins, maleic acid resins, rosin modified maleic acid resins, polyvinyl alcohols, polyvinyl acetals, zein, casein, CMC, shellac, acrylic emulsions, styrene-acryl emulsions, styrene-shellac emulsions and vinyl acetate emulsions.

6. The indicator according to claim 1 attached to a label.

7. The indicator according to claim 1 attached to a tape.

8. The indicator according to claim 1 attached to a test piece.

9. The indicator according to claim 1 attached to a bag.

10. The indicator according to claim 1, wherein an acid catalyst for controlling the reaction between said azo dye and said epoxy compound is further present therein.

11. The indicator according to claim 10, wherein the acid catalyst is at least one member selected from the group consisting of phosphoric acid, p-toluenesulfonic acid, citric acid, maleic acid and malonic acid.

12. The indicator according to claim 1, wherein said undissociative substituent is selected from the group consisting of methyl, ethyl, propyl, butyl, methoxy, ethoxy, propoxy, butoxy, ethylol, methylol, methoxy methyl, phenyl, phenoxy, benzyl and nitro.

13. The indicator according to claim 12, wherein the element of the separating membrane is a member selected from the group consisting of vinyl acetate resins, vinyl chloride resins, ethylene-vinyl acetate copolymer resins, vinyl chloride-vinyl acetate copolymer resins, styrene resins, acrylic resins, polyamide resins, alkyd resins, petroleum resins, coumarone-indene resins, cyclized rubbers, urethane resins, styrene-acryl copolymer resins, styrene-maleic acid copolymer resins, maleic acid resins, rosin modified maleic acid resins, polyvinyl alcohols, polyvinyl acetals, zein, casein, CMC, shellac, acrylic emulsions, styrene-acryl emulsions, styrene-shellac emulsions and vinyl acetate emulsions.

14. The indicator according to claim 13, wherein an acid catalyst for controlling the reaction between an azo dye and an epoxy compound is further present therein.

15. The indicator according to claim 14, wherein the acid catalyst is at least one member selected from the group consisting of phosphoric acid, p-toluenesulfonic acid, citric acid, maleic acid and malonic acid.

16. The indicator according to claim 15, wherein the element (b) of at least one epoxy compound is contained in microcapsules whose shell is the element (c) of a separating membrane.

17. The indicator according to claim 12, wherein the element (b) of at least one epoxy compound is contained in microcapsules whose shell is the element (c) of a separating membrane.

18. The indicator according to claim 17, wherein a uniform mixture of the element (a) of at least one azo dye and the microcapsules is coated on a substrate in the form of a layer.

19. The indicator according to claim 17, wherein the element (a) of at least one azo dye is coated on a substrate in the form of a layer and thereon the microcapsules are coated also in the form of a layer.

20. The indicator according to claim 13, wherein the acid catalyst is at least one member selected from the group consisting of phosphoric acid, p-toluenesulfonic acid, citric acid, maleic acid and malonic acid.

21. The indicator according to claim 20, wherein the element (b) of at least one epoxy compound is contained in microcapsules whose shell is the element (c) of a separating membrane.

22. The indicator according to claim 12, wherein an acid catalyst for controlling the reaction between an azo dye and an epoxy compound is further present therein.

* * * * *